United States Patent [19]
Groiso

[11] Patent Number: 5,993,476
[45] Date of Patent: Nov. 30, 1999

[54] SURGICAL CLIP AND METHOD

[76] Inventor: Jorge A. Groiso, Avachuco 1570 P.9, Buenos Aires 112 -, Argentina

[21] Appl. No.: 09/208,224

[22] Filed: Dec. 9, 1998

Related U.S. Application Data

[63] Continuation of application No. 08/760,112, Dec. 3, 1996.
[51] Int. Cl.$^6$ ....................................................... A61B 17/08
[52] U.S. Cl. ......................... 606/219; 606/213; 606/220; 411/457; 411/920
[58] Field of Search ...................................... 606/213, 219, 606/216, 220; 411/457, 458, 920

[56] References Cited

U.S. PATENT DOCUMENTS

| | | | |
|---|---|---|---|
| 4,444,181 | 4/1984 | Wevers et al. | 128/92 |
| 4,887,601 | 12/1989 | Richards | 606/219 |
| 5,026,390 | 6/1991 | Brown | 606/221 |
| 5,449,359 | 9/1995 | Groiso | 606/75 |

*Primary Examiner*—Michael Buiz
*Assistant Examiner*—Tina T. D. Pham
*Attorney, Agent, or Firm*—Ostrolenk, Faber, Gerb & Soffen LLP

[57] ABSTRACT

A surgical clip for connecting at least two bio-organic tissue members together, the clip comprising a body having two spaced legs and formed into a U-shape, each leg having a distal end which can be inserted into an opening in bone and each having a proximal end, the proximal ends of said at least two legs being connected to corresponding ends of a deformable bridge comprising two spaced apart bridge sections with a gap disposed between the bridge sections, the bridge sections being deformable by a force, the gap being changed by the force to cause the two spaced legs to move into engagement with side walls of the openings in the bone to which the clip is connected, the body comprising the at least two spaced legs and the two bridge sections comprising a single piece of material.

18 Claims, 3 Drawing Sheets

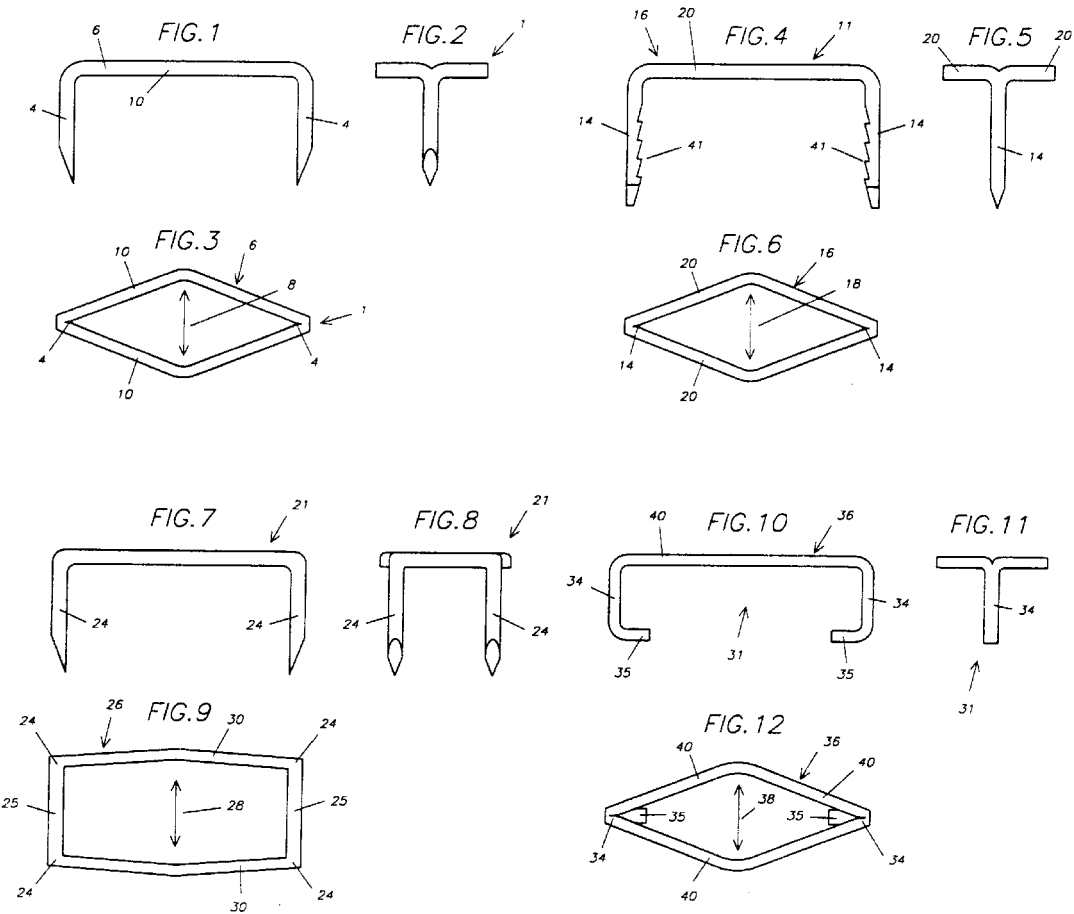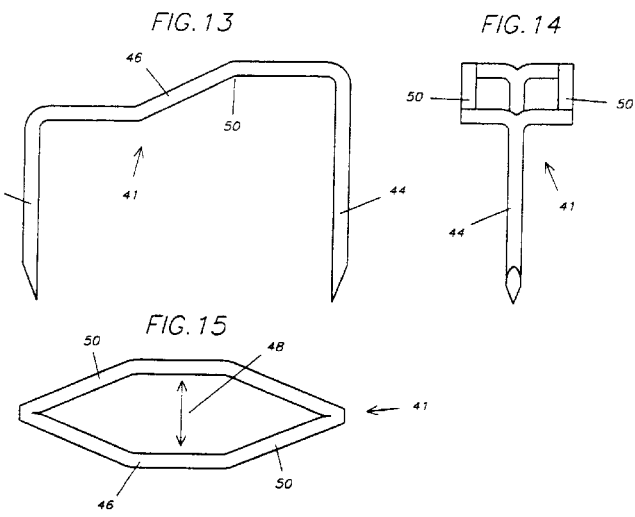

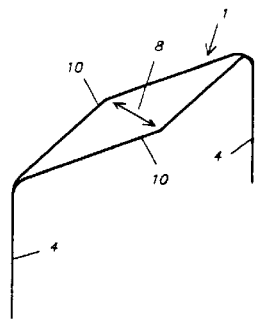
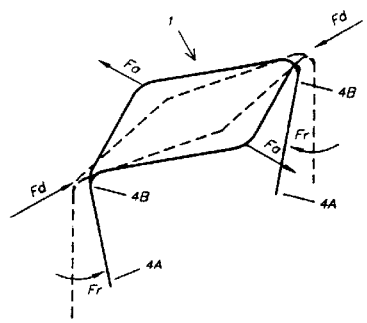
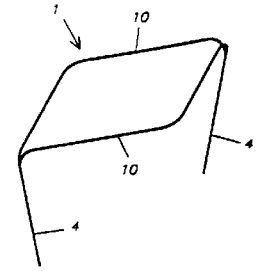
FIG. 16  FIG. 17  FIG. 18
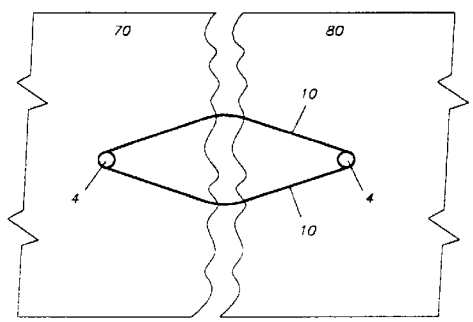
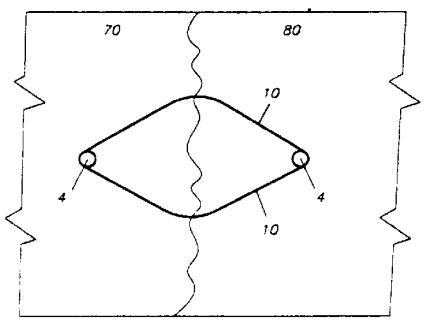
FIG. 19  FIG. 20

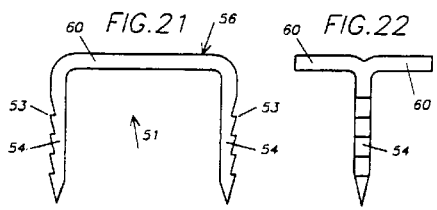
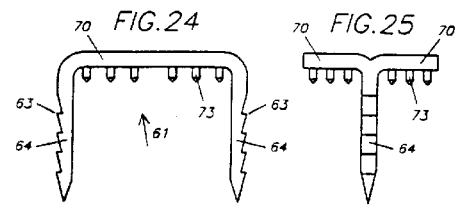
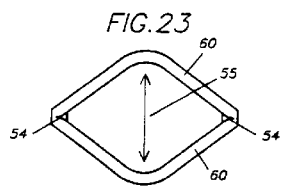
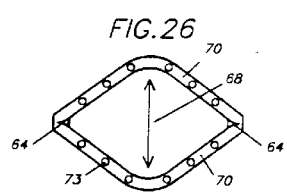
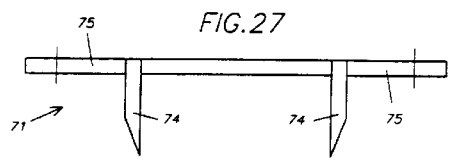
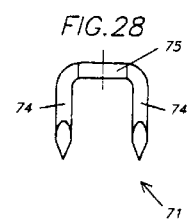
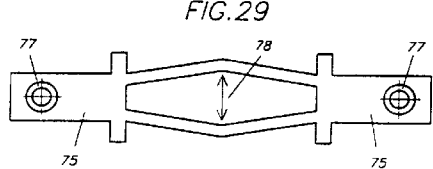
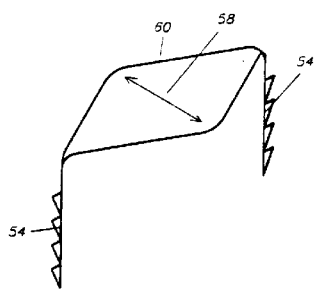
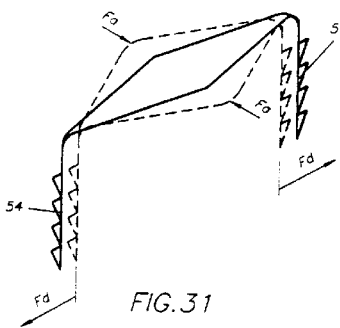
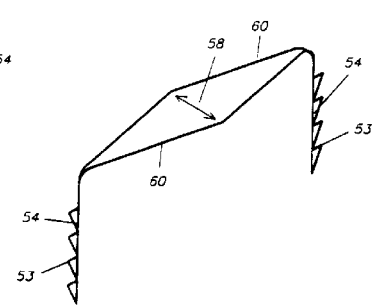

SURGICAL CLIP AND METHOD

This is a continuation of application Ser. No. 08/760,112, filed Dec. 3, 1996.

BACKGROUND OF THE INVENTION

The present invention relates to a clip for surgical procedures, for example, for aiding consolidation or osteosynthesis between bone parts wherein it is necessary to maintain the parts together for the duration of the process of union between them. Furthermore, the present invention also permits two parts of a bone to consolidate properly, correcting any tendency towards malformation thereof. In addition, the clip of the present invention allows ligaments or tendons to be connected to bone parts. More particularly, the present invention relates to a surgical clip that has elastic properties or that is deformable to set the clip in place.

Various devices are known which permit the osteosynthesis of two bone parts or fragments by holding them together and avoiding their movement insofar as possible. Thus, there are external elements such as casts and internal elements such as screws, plates, clips, etc. which perform this function. Argentine Patent 203,977 refers to a curved nail for the treatment of fractures and comprises an elongated body which at one end has a coupling part which is to be inserted into the bone. Types of plates and nails for knitting of femur heads are known from Argentine Patent 212,889 and Argentine Patent 214,240. Connecting plates for two fragments of bones are also known from Argentine Patent 211,803 in which a plate with orifices for screws is placed over the parts to be connected.

Argentine Patent No. 236,884 refers to a fastening clip especially for osteosynthesis and, for its application, the clip must be inserted in the bone by at least one pair of legs while a bridge portion which connects the two legs together remains outside the bone and effects the connection between the two bone fragments. This clip is to be used especially together with a similar clip, each one placed on each adjacent portion of bone to be connected; the bridge portions of the two clips are then connected together by an elastic element which pulls the two bone parts together that are being united.

Applicant's U.S. Pat. No. 5,449,359 discloses an elastic clip for osteosynthesis which is constructed by welding together a plurality of staples. The clip, in one embodiment, has two bridge sections between legs, the bridge sections being separated by a gap. An instrument is inserted into the gap to widen the gap which causes the legs of the clip to move together thereby causing the bone fragments in which the respective legs are inserted to move together.

However, the clip of the above-identified U.S. Patent suffers from the disadvantage that it is made, in the embodiments illustrated in that patent, in a plurality of pieces, thus increasing cost.

Other devices are also known for securing soft tissue, e.g., tendons and ligaments to bone. The tendons or ligaments have to be fastened to the bone through a device that provides enough stability in order to be able to start the rehabilitation treatment as fast as possible. That has been shown in knee surgery; the new fixation systems for surgery of the cruciate ligaments are very strong. There is no need for a plaster cast immobilization, a knee brace is sufficient, and it is removed partially very early to begin motion of the joint, because it has been shown that the motion improves the healing of the tendons or ligaments.

The known devices for soft tissue fixation that are used are:

1) Interference screws, in which a ligament or a tendon is submerged in a hole in the bone, and a screw is applied in that hole. The threads fix the tendon to the wall of the hole. The disadvantage is that when one rotates the screw, the tendon is also rotated, and it can also cut the tendon fibers if the fit is too tight.

2) Screw with a washer with spikes, in which the tightening of the screw drives the spikes from the washer through the tendon fibers, pressing them against the bone. The disadvantage of this system is that the tendon is unevenly pressed, tilting the washer.

3) Anchor, in which a device with two prongs at the end is provided. The other end has two sutures to tie the tendon, which is the weak point of the system.

Although some of the known devices have given generally good results, the surgeon is confronted with the problem that some prior art connecting elements are bulky and complicated which increases the traumatic suffering to which the patient is subjected. Some of the smaller ones, like clips, do not succeed in efficiently fastening the bone portions or tissue members together, because it is not possible to avoid shifting or turning of the bone parts or tissue members with respect to each other. When it is desired to consolidate two bone fragments, it is necessary to have excellent contact between the parts as well as compression between bone ends. Scientific investigations have shown that by suitable compression between the parts to be connected, a faster consolidation of better quality is obtained.

Since it is necessary to work through the wound of the patient in order to place the parts to be connected in contact and fix them, it is preferred that the connecting means be as simple as possible. It is also preferred that the connecting elements be as simple as possible to fix in position, and require as little time as possible to set, in order to minimize trauma.

In the prior art, there are simple clips of U-shape which are very similar to those clips which are used in paper staplers. These U-shaped clips have sharpened ends which are inserted in a bone portion and they maintain their position by the rigid structure of the legs of the U-shape. However, these conventional clips maintain the same distance between the bone fragments and, therefore, if there is not coaptation, there is instability in rotation, which means that the bone portions may turn with respect to each other and may even separate. This phenomenon would not occur if one succeeded in maintaining the bone ends compressed against each other.

In the contrary case, in which it is desired to maintain a degree of separation between the bone fragments, which case is particularly useful for bone malformation correction, there are no clips known to applicant, other than applicant's clip described in U.S. Pat. No. 5,449,359, which make it possible to obtain this spacing, and therefore, it would be very useful to have clips which make it possible to achieve this at reduced cost. The clip of U.S. Pat. No. 5,449,259 can achieve this but it is desirable to improve on that clip by providing such a clip of reduced cost.

As stated above, the aim of attaining a desired spacing between bone fragments could be obtained with connecting elements such as plates and screws, but these are much bulkier, require major surgical procedures for the placing thereof and the possibility of trauma is increased.

In addition to the surgical use of the invention, it is also possible to use the invention in non-surgical areas, e.g., construction, woodworking, the general fastener industry, etc.

SUMMARY OF THE INVENTION

It is an object of the present invention to provide a surgical clip for osteosynthesis which solves the problems mentioned above, i.e., avoids that once the clip is put in place, the bone fragments move with respect to each other and, in contrast, maintains the ends of the bone fragments in a compressed, connected state without the necessity of complicated and bulky parts which would require traumatic major surgical procedures.

A further object of the present invention is to provide a surgical clip which is able to maintain a specified separation between bone fragments to which the clip is attached.

Yet still a further of the present invention is to provide a surgical clip which is simpler to manufacture than the device disclosed in applicant's U.S. Pat. No. 5,449,359.

A further object of the present invention is to provide a surgical clip useful for fastening soft tissue members such as ligaments and tendons to bone parts.

The above and other objects of the present invention are achieved by a surgical clip for connecting at least two bio-organic tissue members together, the clip comprising a body having two spaced legs and formed into a U-shape, each leg having a distal end which can be inserted into an opening in bone and each having a proximal end, the proximal ends of said at least two legs being connected to corresponding ends of a deformable bridge comprising two spaced apart bridge sections with a gap disposed between the bridge sections, the bridge sections being deformable by a force, the gap being changed by the force to cause the two spaced legs to move into engagement with side walls of the openings in the bone to which the clip is connected, the body comprising the at least two spaced legs and the two bridge sections comprising a single piece of material.

Other objects, features and advantages of the present invention will become apparent from the following description of the invention which refers to the accompanying drawings.

BRIEF DESCRIPTION OF THE DRAWINGS

For greater clarity and understanding, he present invention has been shown in various figures in which it is illustrated in its preferred embodiments, all by way of illustration and not of limitation, and in which:

FIG. 1 is a side elevation of a preferred embodiment of the clip of the invention;

FIG. 2 is an end view in elevation of the clip of FIG. 1;

FIG. 3 is a top plan view of the clip of FIG. 1;

FIG. 4 is a side view of another embodiment of the clip according to the present invention;

FIG. 5 is an end view of the clip of FIG. 4;

FIG. 6 is a top plan view of the clip of FIG. 4;

FIG. 7 is a side view of another embodiment of the clip of the invention;

FIG. 8 is an end view of the clip of FIG. 7;

FIG. 9 is a top plan view of the clip of FIG. 7;

FIG. 10 is a side view of yet still another embodiment according to the present invention;

FIG. 11 is an end view of the clip of FIG. 10;

FIG. 12 is a top plan view of the clip of FIG. 10;

FIG. 13 is a side view of yet still a further embodiment of the clip according to the present invention;

FIG. 14 is an end view of the clip of FIG. 13;

FIG. 15 is a top plan view of the clip of FIG. 13;

FIG. 16 is a perspective view of the clip of FIG. 1;

FIG. 17 is a schematic drawing in perspective view illustrating the forces applied to the clip of FIG. 16 and showing the translations of various portions of the clip and illustrating how the invention achieves compression;

FIG. 18 is a perspective view of the clip according to FIG. 16 after a force has been applied to the clip to secure it;

FIG. 19 is a schematic top view corresponding to FIG. 16 showing a clip in position in two bone fragments but prior to applying a force to achieve compression;

FIG. 20 is a schematic top view of the clip of FIG. 18 showing a clip in position in two bone fragments after a force has been applied to achieve compression between the fragments;

FIG. 21 is a side elevation of a further embodiment according to the present invention;

FIG. 22 is an end view in elevation of the clip of FIG. 21;

FIG. 23 is a top plan view of the clip of FIG. 21;

FIG. 24 is a side elevation of yet still a further embodiment according to the present invention;

FIG. 25 is an end view in elevation of the clip of FIG. 24;

FIG. 26 is a top plan view of the clip of FIG. 24;

FIG. 27 is a side elevation of yet still a further embodiment of the clip of the invention;

FIG. 28 is an end view in elevation of the clip of FIG. 27;

FIG. 29 is a top plan view of the clip of FIG. 27;

FIG. 30 shows in schematic perspective view the clip of FIG. 21 prior to emplacement;

FIG. 31 is a diagram showing the forces applied to the clip of FIG. 30 to emplace it and the movements of portions of the clip; and FIG. 32 shows the clip of FIG. 30 after emplacement.

DETAILED DESCRIPTION OF EMBODIMENTS OF THE INVENTION

With reference now to the drawings, it should be pointed out that in the different embodiments, the reference numbers used in FIG. 1 will be used for equivalent parts of the embodiments of the different figures with the same digit but increased by 10. Thus, the embodiment of FIGS. 1, 2 and 3 will be identified by the number 1 while the following embodiment of FIGS. 4, 5 and 6 will bear the number 11, and the embodiment of FIGS. 7, 8 and 9 will bear the number 21, etc.

Referring to FIG. 1, there is shown a surgical clip in accordance with the present invention in side view. As appears more clearly from viewing FIGS. 1, 2 and 3 together, the clip 1 is formed of a single piece of a biocompatible material. The clip is formed preferably from a sheet of a biocompatible metal, for example stainless steel 316L. Preferably, the clip is formed out of the sheet of metal using a laser beam cutter or other technique which provides a fine cut. After the clip is cut out of the sheet of metal, the clip is bent into the U-shape shown in FIG. 1 such that vertical legs 4 are provided to the clip to give it the U-shape. As shown in FIG. 3, the clip 1 is cut out of the sheet metal so as to have a bridging portion 6 which comprises two adjacent elongated bridge sections 10 spaced from each other by a gap 8. The gap 8 can be formed when the clip 1 is cut from the sheet of metal or thereafter by spreading the sections 10 to create the gap 8.

Once the clip 1 has been cut from the metal and the legs bent and formed into the U-shape and the gap 8 formed, it is then preferably polished, for example, using a shot peening technique or an electrolytic technique.

As shown in FIGS. 16–20, to utilize the surgical clip according to the embodiment of FIGS. 1–3 for the osteosynthesis of two bone parts, the legs 4 are inserted into respective bore holes formed in bone members 70 and 80, as shown in FIG. 19. A tool, such as a pair of pliers, and illustrated in applicant's U.S. Pat. No. 5,449,359, is then inserted into the gap 8, causing the gap 8 to be increased. This is shown in FIG. 17 where a force Fa has been indicated extending in the directions shown causing the gap 8 to increase from the gap shown in phantom in FIG. 17 to the gap width indicated by the solid lines of FIG. 17 and also shown in FIG. 18. As shown in FIG. 20, the increase in the width of the gap 8 causes the legs 4 to be drawn together which causes bone fragments 70 and 80 to be drawn together closely, decreasing the gap G (FIG. 19) between the bone fragments and therefore allowing osteosynthesis to occur.

When the force Fa is applied to the clip according to the present invention to expand the gap 8 between the bridge sections 10, the legs 4 move together thereby to cause the gap between the bone fragments to decrease. As a result of the increase of the gap 8 between the bridge sections 10, the legs 4 translate towards each other unevenly (by pivoting about their connections to the bridge sections 10), so that the distal portions of the legs 4A move more closely together than the proximal portions of the legs 4B as illustrated in FIG. 17. As shown there, the translation of distal portions 4A of the legs is greater than the translation of the proximal portions 4B of the legs. This causes the bone fragments 70 and 80 to be drawn into tight compression with each other and minimizes the possibility of extrusion of the clip from the bone.

An important aspect of the invention is that the elastic clip is made from a single piece of metal, for example, from a piece of sheet metal, for example, by a laser beam or other means which provides a clean finished surface. Other means can also be employed, for example, stamping, die casting, machining or plasma cutting. However, it has been found that the use of a laser beam to cut the clips out of a sheet of biocompatible metal, for example stainless steel, has provided the best and most economical results. However, it is not necessary that a laser beam cutter be used. Other means can also be used provided it achieves a clip made out of one piece of metal.

According to the invention, the clip can also be employed for the securement of soft tissue, for example, tendons or ligaments to bone. To use the clip of the invention to secure soft tissue to bone, two boreholes of appropriate widths to provide a snug fit with legs 4 and of appropriate lengths to receive legs 4 are made in the intact bone where the tendon or ligament is to be attached. The two legs 4 of the clip according to the invention are pressed into the holes, for example with a hammer, about half way. The tendon or ligament is then slid underneath the bridge sections 10 and held with the proper tension, and the clip is then forced, for example with a hammer, the rest of the way into the holes in the bone. Then the spacing between the bridge sections 10 is either increased or decreased to cause the legs 4 to securely grip the bone. The spacing 8 can be decreased, in which case, the legs 4 move away from each other, but still securely are pressed against the walls of the hole in the bone. The tendon or ligament is thus secured beneath the bridge sections 10. Little movement of the bridge sections 10 to change the gap spacing 8 is necessary.

As will be explained in more detail below, in the preferred embodiment of the clip for securing ligaments or tendons to bone, the legs of the clip are provided with teeth or serrations to grip the bone, and instead of increasing the gap 8 between the bridge sections, the gap is decreased to cause the legs to move apart from each other. In addition, teeth or serrations are preferably provided extending distally on the underside of the bridge sections 10 to engage the soft tissue in this embodiment. This will be described in greater detail below. However, each of the embodiments described are also capable of being used to secure soft tissue to bone.

FIGS. 4, 5 and 6 show a second embodiment according to the present invention. The clip 11 is substantially the same as the embodiment of FIGS. 1, 2 and 3. The only difference is that serrated teeth 41 have been provided along the inside facing portions of the legs 14 whereby to allow the legs 14 to tightly grip the bone fragment into which they are inserted.

FIGS. 7, 8 and 9 show still yet another embodiment according to the present invention. In this embodiment, a clip 21 is formed in plan view in substantially the shape of a rectangle, possibly with a slight bow shape so that the gap 28 is widest at the center. At each corner of the rectangle, legs 24 are disposed. The legs 24 at each end are connected by a transverse section 25. The bridge sections 30 of the elongated bridge portion 26 are spaced apart by a gap 28, which like in the embodiments of FIGS. 1–3 and 4–6, is increased to cause the legs 24 to be moved together to cause the compression effect shown in FIGS. 16–20 and which causes the bone fragments 70 and 80 to be drawn together.

As in the other embodiments, the clip 21 is preferably formed from one piece of metal, preferably sheet metal and thereafter bent into the U-shape shown.

FIGS. 10, 11 and 12 show yet another embodiment according to the present invention. In this embodiment, the surgical clip 31 is formed similarly to the embodiment of FIGS. 1–3. However, the downwardly depending legs 34 include horizontally formed tips 35 which extend toward each other. In this embodiment, the clip 31 having the tips 35, for example, extending for about 1 to 2 mm, is useful to close flat bones like the sternum after thoracic surgery. Additionally, as shown in the embodiment of FIGS. 10, 11 and 12, the tips 35 of the legs 34 may be formed without sharp ends. As shown in the other already described embodiments, the legs 4, 14 and 24 all have been provided with sharp ends to assist in emplacement of the legs in the boreholes in the bone. Alternatively, the clip of the invention may also be used, in appropriate circumstances, as a self-tapping clip wherein the clip is driven into the bone with a hammer, thereby forming its own borehole. In this case, there is no need to drill boreholes in advance.

In the embodiment shown in FIGS. 4, 5 and 6, the serrations or spikes on each leg facing the opposed leg grab the borehole in the bone or the edges of the bone, thereby preventing extrusion or removal of the clip when it is installed. (The clip can be removed purposely only by altering the gap spacing between bridge sections with an appropriate tool). This is an additional means of achieving a firm fixation of the clip in the bone, in addition to the convergent or twisting motion of the legs described with respect to FIGS. 16–20, i.e., the greater displacement of tips 4B than portion 4A of the legs.

FIGS. 13, 14 and 15 show another embodiment according to the present invention. In this clip 41, the bridge sections 50 of the bridging portion 46 are each provided with a step so that the legs 44 are of different lengths. This may be useful to fix bones of different thicknesses. As shown in FIG. 15, the embodiment of FIGS. 13–15 may also be formed substantially similarly, in plan view, to the embodiment of FIGS. 1–3, 4–6 and 10–12.

The clip according to the invention is preferably made of a suitable biocompatible material which is of good elasticity and good mechanical strength. Materials of this type which are suitable for use in the present invention are, for instance, titanium alloy metals such as Ta6V of medical grade or stainless steels of medical grade, such as 316L. Other materials, including non-metallic biocompatible materials, can also be used. Furthermore, the clip may be made of a suitable bioabsorbable material, in which case, the clip is absorbed by the body after healing of the bone parts.

Although the present invention may be employed by drilling a hole in each of the two bones to be held together and inserting respective legs of a clip into the boreholes, the invention may also be used so that the legs extend around the bone fragments to be held together. The embodiment of FIGS. 10–12 is particularly suited for this purpose.

In contrast to the use of the invention for holding two bone fragments together, the clip of the present invention may also be used in applications where it is desired to maintain a degree of separation between the bone ends to be connected. This is necessary in some cases in which a correction is desired in a bone piece which otherwise would consolidate and even grow in a manner other than that desired. The clip of the invention would be placed in the bone pieces as described previously but instead of separating the elongated bridge sections, for example sections 10, 20, 40 or 50, the gap in the bridging portion is decreased by compressing the bridge sections 10, 20, 40 or 50 together so as to produce a movement apart between the legs 4, 14, 34 or 44 of the ends of the clip 1, 11, 31 or 41.

With respect to the embodiment shown in FIGS. 7, 8 and 9, in this embodiment, where the plan view of the clip is a true rectangle, it is only possible to move the legs 24 at each end of clip 21 substantially together since both an expansion and decrease in the size of the opening 28 will cause the legs 24 at opposed ends of the clip to move toward each other. In order to allow the clip of the embodiment of FIGS. 7, 8 and 9 to be used to cause separation, the gap 28 must be increased at the center beyond the transverse dimension T of sections 25. This will allow a decrease of gap 28 to cause opposed legs 24 to move apart.

FIG. 21 shows yet still another embodiment according to the present invention. In this embodiment, clip 51 has legs 54 provided with teeth or serrations 53 on the outside facing portions of the legs 54. In this embodiment, the spacing 58 between the bridge section 60 is preferably enlarged, as compared to the embodiment of e.g., FIGS. 1–3. To emplace the clip 51, according to FIGS. 21–23, the gap 58 is decreased, causing the legs to move apart, thus securely engaging the outer serrated portions of legs 54 with the boreholes in which the legs are secured. This clip is particularly suited for the connection of soft tissues, for example ligaments and tendons, to bone. In this case, the clip 51 is driven partially into the holes in the bone. The tendon or ligament is then slid underneath the bridge sections 60 and the clip is driven the rest of the way into the bone, thereby securing the tendon or ligament under the bridge sections 60. The gap 58 is then decreased, causing the serrations 53 in the legs 54 to securely engage the bone, thereby securing the tendon or ligament in the bone.

FIGS. 24–26 show a preferred embodiment of the clip useful for securing soft tissues to bone. In this embodiment, indicated by the designation 61, the clip includes a plurality of teeth or serrations 73 spaced downwardly or distally from bridge sections 70. The legs 64 include serrations or teeth 63. After the tendon or ligament is disposed beneath the bridge sections 70 of the clip 61 and the clip is driven the rest of the way into the bone, the teeth or serrations 73 on the underside of the bridge sections 70 will penetrate the fibers of the tendon or ligament and secure it against the bone. The spacing 68 between the bridge sections 70 is then decreased. Because the bone is intact, little motion is needed when decreasing the spacing 68, to cause the lateral serrations or teeth 63 in the legs 64 to impact against the sides of the bore holes. A very secure fixation of the tendon or ligament is thus provided by the embodiment of FIGS. 23–26.

FIG. 27 shows a further embodiment of the clip according to the invention. In this embodiment, the clip is formed much as the embodiment of FIGS. 7–9. However, in this embodiment, generally indicated by the reference numeral 71, laterally extending wings 75 are provided. These laterally extending wings each contain an aperture 77 therein for the provision of a screw to provide increased securement of the clip to the bone. This embodiment can be used both for osteosynthesis of two bone parts in which the two bone parts are desired to be brought together by causing the gap 78 to be enlarged and also in a situation where it is desired to maintain a spacing between the bone parts in which case the gap 78 may be decreased in size. This will cause the legs 74 at opposite sides of the clip to move apart. The clip of FIGS. 27–29 may also be used to secure soft tissues to bone in the same way as described above. The gap 78 may either be enlarged or decreased to cause the securement, and once the clip has been emplaced, screws are provided through the openings 77 to further secure the clip into the bone.

FIGS. 30–32 show the clip of FIGS. 21–23 and 24–26 schematically. FIG. 30 shows the clip prior to emplacement. FIG. 32 shows the clip after emplacement in which the gap 58 has been decreased to cause the legs 54, as shown in FIG. 31, to move apart from each other. The teeth or serrations 53 thereby engage in the boreholes into which the legs 54 have been inserted to securely hold the clip in the bone. As shown in FIG. 31, a force Fa has been provided to decrease the spacing 58 from the initial spacing shown in phantom to the spacing shown in the solid line. This results in a movement in the direction Fd of each of the legs 54 away from each other.

As the present invention has been described with respect to particular embodiments thereof, many other variations and modification and other uses will become apparent to those skilled in the art. Therefore, the present invention should be limited not by the specific disclosure herein, but only by the appended claims.

What is claimed is:

1. A surgical clip for connecting at least two bio-organic tissue members together, the clip comprising a body having two spaced legs and formed into a U-shape, each leg being substantially straight, each leg having a distal end which can be inserted into an opening in a bio-organic tissue member and each having a proximal end, the proximal ends of said at least two legs being connected to corresponding ends of a deformable bridge coupling the at least two legs together, the bridge comprising two spaced apart bridge sections with a gap disposed between the bridge sections, the bridge sections having a non-deformed condition and a deformed condition, the bridge sections being deformable by a force such that once the bridge sections are deformed, the bridge sections remain in the deformed condition and do not automatically return back to the non-deformed condition, the gap being changed by the force to cause the two spaced legs to move, when the clip is inserted into the two bio-organic tissue members, into secure engagement with side walls of the openings in the bio-organic tissue members to which the clip is connected, the body comprising the at least two spaced legs and the two bridge sections comprising a single piece of bio-compatible material formed from a sheet of metal in a single piece and bent into the U-shape, distal portions of the spaced legs moving closer together than proximal portions of the spaced legs when the gap between the bridge sections is increased, the legs remaining substantially straight after the gap between the bridge sections is increased without having distal portions of the spaced legs bent at an angle to a longitudinal axis of the spaced legs, thereby securely holding the two tissue members together.

2. The clip of claim 1, wherein the gap is increased to cause the two spaced legs to move toward each other thereby to cause the tissue members to which the clip is connected to be drawn together.

3. The clip of claim 1, wherein the single piece of material comprises a biocompatible metal.

4. The clip of claim 1, wherein the legs have serrations for causing the legs to tightly grip the tissue members.

5. The clip of claim 4, wherein the serrations on each leg face each other.

6. The clip of claim 1 wherein the bridge sections are separated by a gap along their length at a widest portion and are connected to each other at ends thereof to form a leg at each end.

7. The clip of claim 1, wherein the legs further comprise a tip portion extending transversely therefrom substantially parallel to the bridge sections.

8. The clip of claim 1, wherein the bridge sections include a step portion so that the legs are of different lengths.

9. The clip of claim 1, further wherein the gap between the bridge sections may be decreased to cause the legs to move apart, thereby to maintain a spacing between the tissue members.

10. The clip of claim 3, wherein the single piece of material comprises a piece of metal cut from sheet metal.

11. The clip of claim 10, wherein the single piece of metal is cut with a laser beam.

12. The clip of claim 3, wherein the biocompatible metal comprises one of a stainless steel and a titanium alloy.

13. The clip of claim 1, further wherein the single piece of metal is shot peened to provide a suitable finish.

14. The clip of claim 1, wherein the clip comprises a bioabsorbable material.

15. The clip of claim 4, wherein the serrations on each leg face away from each other.

16. The clip of claim 15, wherein the gap between the bridge sections is decreased to cause the legs to move apart thereby to cause the serrations on the legs to tightly grip the tissue members.

17. A surgical clip for connecting at least first and second bio-organic tissue members together, the clip comprising a body having two spaced legs and formed into a U-shape, each leg being substantially straight, each leg having a distal end which can be inserted into an opening in at least the first bio-organic tissue member and each having a proximal end, the proximal ends of said at least two legs being connected to corresponding ends of a deformable bridge coupling the at least two legs together, the bridge comprising two spaced apart bridge sections with a gap disposed between the bridge sections, the bridge sections being deformable by a force, the gap being changed by the force to cause the two spaced legs to move, when the legs of the clip are inserted into openings in the at least first bio-organic tissue member, into secure engagement with side walls of the openings in the at least first bio-organic tissue member, the body comprising the at least two spaced legs and the two bridge sections comprising a single piece of bio-compatible material formed from a sheet of metal in a single piece and bent into the U-shape, distal portions of the spaced legs moving closer together than proximal portions of the spaced legs when the gap between the bridge sections is increased, the legs remaining substantially straight after the cap between the bridge sections is increased without having distal portions of the spaced legs bent at an angle to a longitudinal axis of the spaced legs, thereby securely holding the two tissue members together; and wherein the surgical clip is adapted to couple the second bio-organic tissue member comprising a soft tissue member to the first tissue member, the deformable bridge having an underside adapted to grasp the soft tissue member, the first tissue member comprising a bone member, the soft tissue member being receivable between the underside of the deformable bridge and the bone member when the clip is provided into the openings in the bone member.

18. The clip of claim 17, wherein the bridge sections have teeth or serrations extending distally for engagement with a soft tissue member secured between the deformable bridge and the bone member.

\* \* \* \* \*